United States Patent [10] Patent No.: US 11,779,397 B2
Koett et al. [45] Date of Patent: Oct. 10, 2023

(54) BIOLOGICAL TISSUE POSITION LOCATION AND MARKING

(71) Applicant: AtriCure, Inc., Mason, OH (US)

(72) Inventors: Heidi Koett, Loveland, OH (US);
Matthew Monti, Cincinnati, OH (US);
Salvatore Privitera, Mason, OH (US)

(73) Assignee: AtriCure, Inc., Mason, OH (US)

( * ) Notice: Subject to any disclaimer, the term of this patent is extended or adjusted under 35 U.S.C. 154(b) by 500 days.

(21) Appl. No.: 16/869,157

(22) Filed: May 7, 2020

(65) Prior Publication Data
US 2020/0352656 A1 Nov. 12, 2020

Related U.S. Application Data

(60) Provisional application No. 62/845,313, filed on May 8, 2019.

(51) Int. Cl.
*A61B 34/20* (2016.01)
*A61B 90/00* (2016.01)
(Continued)

(52) U.S. Cl.
CPC .............. *A61B 34/20* (2016.02); *A61B 18/02* (2013.01); *A61B 18/1815* (2013.01);
(Continued)

(58) Field of Classification Search
CPC ..... A61B 34/20; A61B 18/02; A61B 18/1815; A61B 18/20; A61B 18/1492; A61B 90/39; A61B 2018/00357; A61B 2018/00363; A61B 2018/00577; A61B 2018/00351; A61B 2018/00875; A61B 2034/2051;
(Continued)

(56) References Cited

U.S. PATENT DOCUMENTS 4,916,170 A 4/1990 Nambu et al.
5,879,357 A 3/1999 Heaton et al.
(Continued)

FOREIGN PATENT DOCUMENTS

JP H10-033547 2/1998
JP 2015-513408 5/2015
(Continued)

OTHER PUBLICATIONS

Aspen Surgical, Endoscopic Kittner, Apr. 14, 2015, 2 pages, https://www.aspensurgical.com/files/resources/copy_of_kittner_brochure_m-sm-cat_-_1014673_-_1_-_.pdf.
(Continued)

*Primary Examiner* — Peter Luong
(74) *Attorney, Agent, or Firm* — Dorton & Willis LLP; Ryan Willis

(57) ABSTRACT

Methods of performing surgical operations and associated devices are disclosed. An example method may include locating a first position on a first surface of a biological tissue; locating a second position on a second opposing surface of the biological tissue, the second position corresponding to the first position; and marking the second position on the second surface. The second surface may be generally opposite the first surface. An example method may include, after marking the second position, performing a therapeutic procedure on the biological tissue in the vicinity of the second position.

41 Claims, 15 Drawing Sheets

(51) Int. Cl.
  *A61B 18/20* (2006.01)
  *A61B 18/18* (2006.01)
  *A61B 18/02* (2006.01)
  *A61B 18/00* (2006.01)

(52) U.S. Cl.
  CPC .............. *A61B 18/20* (2013.01); *A61B 90/39* (2016.02); *A61B 2018/00357* (2013.01); *A61B 2018/00363* (2013.01); *A61B 2018/00577* (2013.01); *A61B 2034/2051* (2016.02); *A61B 2034/2059* (2016.02); *A61B 2090/3966* (2016.02)

(58) Field of Classification Search
  CPC .... A61B 2034/2059; A61B 2090/3966; A61B 2090/392; A61B 2090/3933; A61B 2090/395; A61B 2090/3954; A61B 2090/3987; A61B 17/205; A61B 17/3478; A61B 2017/00053; A61B 2017/00026; A61B 2017/00243; A61B 2017/00247
  See application file for complete search history.

(56) References Cited

U.S. PATENT DOCUMENTS

| | | | |
|---|---|---|---|
| 5,902,310 | A | 5/1999 | Foerster et al. |
| 5,909,978 | A | 6/1999 | Giordano et al. |
| 6,030,377 | A | 2/2000 | Linhares et al. |
| 6,512,943 | B1 | 1/2003 | Kelcz |
| 6,654,629 | B2 | 11/2003 | Montegrande |
| 6,743,228 | B2 | 6/2004 | Lee et al. |
| 6,972,022 | B1 | 12/2005 | Griffin |
| 6,994,712 | B1 | 2/2006 | Fisher et al. |
| 7,044,957 | B2 | 5/2006 | Foerster et al. |
| 7,329,414 | B2 | 2/2008 | Fisher et al. |
| 7,497,862 | B2 | 3/2009 | Viola |
| 8,486,028 | B2 | 7/2013 | Field |
| 8,966,735 | B2 | 3/2015 | Bolan et al. |
| 9,743,970 | B2 | 8/2017 | Euteneuer et al. |
| 9,901,415 | B2 | 2/2018 | Casanova et al. |
| 10,172,674 | B2 | 1/2019 | Jones et al. |
| 10,299,881 | B2 | 5/2019 | Burbank et al. |
| 10,500,014 | B2 | 12/2019 | Hermann et al. |
| 2004/0082850 | A1* | 4/2004 | Bonner ............ A61B 5/06 600/424 |
| 2004/0176759 | A1 | 9/2004 | Krishnamurthy et al. |
| 2005/0288667 | A1 | 12/2005 | Thompson et al. |
| 2006/0217699 | A1 | 9/2006 | Wang et al. |
| 2006/0247516 | A1 | 11/2006 | Hess et al. |
| 2008/0009718 | A1 | 1/2008 | Zohman |
| 2008/0071208 | A1 | 3/2008 | Voegele et al. |
| 2008/0208182 | A1 | 8/2008 | Lafontaine et al. |
| 2009/0076535 | A1 | 3/2009 | Agrawal et al. |
| 2009/0217932 | A1 | 9/2009 | Voegele |
| 2010/0113920 | A1 | 5/2010 | Foerster et al. |
| 2011/0021888 | A1 | 1/2011 | Sing et al. |
| 2012/0191081 | A1* | 7/2012 | Markowitz ........ A61B 18/02 606/21 |
| 2012/0302935 | A1 | 11/2012 | Miller et al. |
| 2012/0316555 | A1 | 12/2012 | Orszulak et al. |
| 2013/0109945 | A1 | 5/2013 | Harlev et al. |
| 2013/0245681 | A1 | 9/2013 | Straehnz et al. |
| 2015/0105729 | A1 | 4/2015 | Valeti et al. |
| 2015/0245883 | A1 | 9/2015 | Talpade et al. |
| 2018/0344425 | A1 | 12/2018 | Burbank et al. |
| 2019/0029560 | A1 | 1/2019 | Harmer et al. |

FOREIGN PATENT DOCUMENTS

| | | |
|---|---|---|
| JP | 2017-213348 | 12/2017 |
| JP | 2018-023786 | 2/2018 |
| KR | 20140006171 | 12/2014 |
| WO | 2013116439 | 8/2013 |
| WO | 2017212617 | 12/2017 |
| WO | PCT/US2020/031889 | 9/2020 |

OTHER PUBLICATIONS

European Patent Office, extended European search report in EP 20803049, dated Dec. 23, 2021.

Japan Patent Office, Notice of Reasons for Rejection in JP 2021-502754, dated Aug. 1, 2022.

* cited by examiner

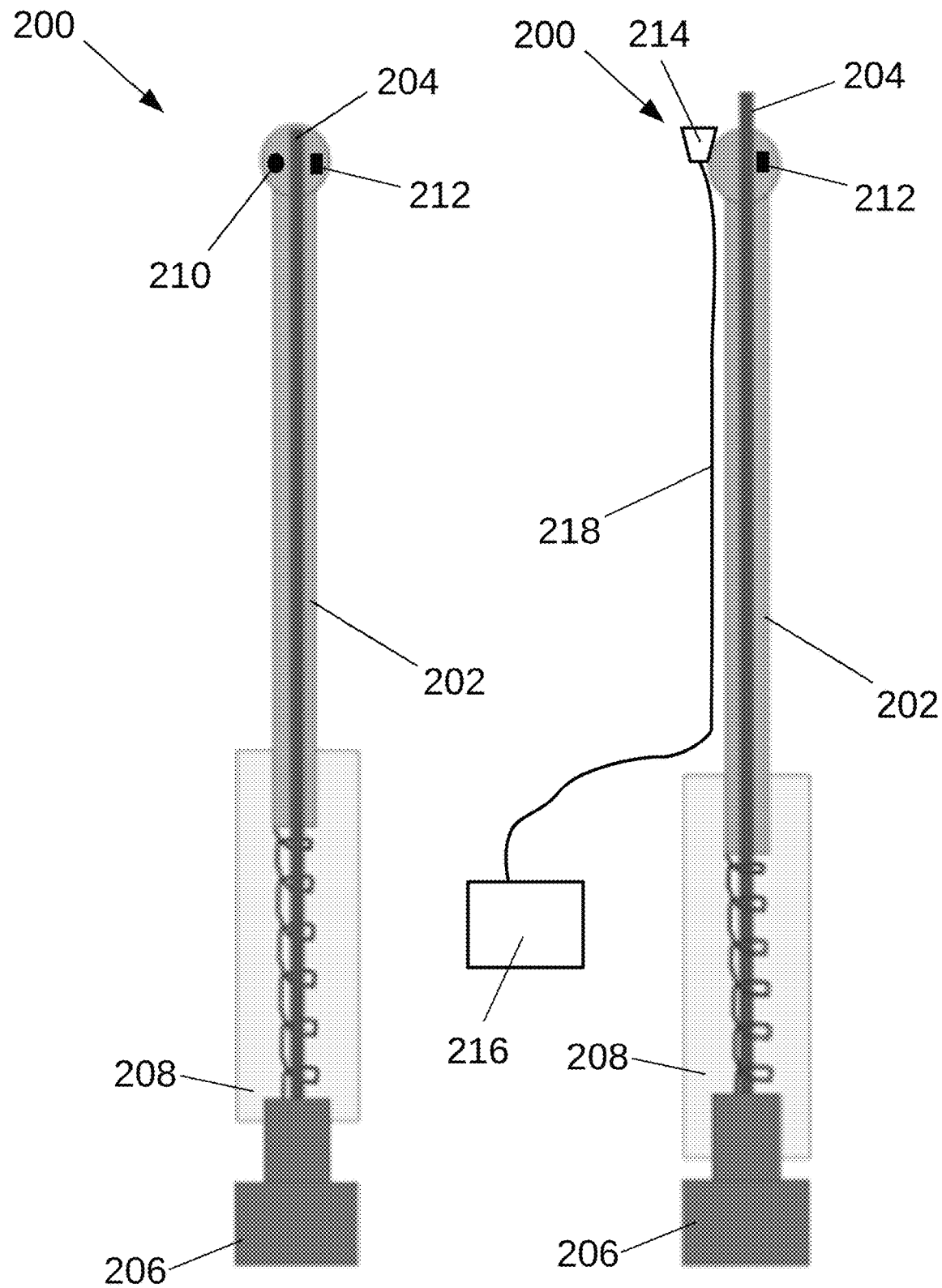
FIG. 12                    FIG. 13

BIOLOGICAL TISSUE POSITION LOCATION AND MARKING

CROSS REFERENCE TO RELATED APPLICATIONS

This application claims the benefit of U.S. Provisional Application No. 62/845,313, filed May 8, 2019, which is incorporated by reference.

INTRODUCTION TO THE INVENTION

The present disclosure is directed to medical instruments and devices and related methods, and, more specifically, to surgical devices for locating and/or marking positions on biological tissues, such as the wall of the heart, and related methods.

The present disclosure contemplates that some cardiac procedures may be performed substantially entirely from within the chambers of the heart, such as by a cardiac electrophysiologist using a catheter-based procedure. The present disclosure contemplates that other cardiac procedures may be performed substantially entirely from the exterior of the heart, such as by a cardiac surgeon accessing the heart via a skin incision. The present disclosure contemplates that a hybrid cardiac surgical procedure may combine an interventional aspect (e.g., an endocardial approach via a catheter guided by fluoroscopy) with a surgical aspect (e.g., an epicardial approach via a skin incision guided by direct visualization or endoscopic camera).

The present disclosure contemplates that surgical pens may be used to mark on a patient's skin; however, surgical pens are generally not optimal for internal use during surgical procedures. For example, the ink used in a surgical pen may rub or brush off of internal structures during the surgical procedure. Further, surgical pens are generally not configured for use during minimally invasive procedures. For example, surgical pens typically do not have appropriate dimensions to facilitate insertion into a surgical site via a thoracoscopic trocar.

SUMMARY

It is an aspect of the present disclosure to provide a method of performing an operation, including locating a first position on a first surface of a biological tissue; locating a second position on a second surface of the biological tissue, the second position corresponding to the first position; and/or marking the second position on the second surface.

In a more detailed embodiment, locating the second position on the second surface may include electrically locating the second position on the second surface. Electrically locating the second position on the second surface may include emitting an electromagnetic signal by an instrument on the second surface, the instrument on the second surface including a sensor configured to detect changes in a signal amplitude influenced by an instrument on the first surface. Electrically locating the second position on the second surface may include measuring a closed-loop impedance between an instrument on the second surface and an opposing instrument on the first surface. Locating the second position on the second surface may include visually locating the second position on the second surface. Locating the second position on the second surface may include mechanically locating the second position on the second surface. Locating the second position on the second surface may include magnetically locating the second position on the second surface.

In a more detailed embodiment, the second surface may be generally opposite the first surface. The method may include, after marking the second position, performing a therapeutic procedure on the biological tissue in the vicinity of the second position. Performing the therapeutic procedure may include ablating a portion of the biological tissue. Marking the second position may include marking a point on the second surface. Marking the second position may include marking a line on the second surface. Marking the second position may include marking an area on the second surface. Marking the area may include marking a perimeter of the area. Marking the area may include marking substantially all of an internal area defined by the perimeter. Marking the second position may include disposing a marker on the second surface. The marker may include a marking substance. The marking substance may include at least one of an ink and a dye. The marking substance may include a radionuclide. The marking substance may include a radiopaque substance. The marking substance may include a magnetic substance. The marker may include an object. The object may include a magnetic substance. The object may be electrically insulative and/or the method may include applying RF energy to the tissue while at least a portion of the tissue is protected from the RF energy by the marker. The object may be bioabsorbable. Disposing the marker on the second surface may include at least partially penetrating the second surface. Locating the second position may be performed without penetrating the biological structure. Marking the second position may include heating the tissue to create a lesion that is detectable on the second surface. Heating the tissue may include applying RF energy, microwave energy, and/or laser energy. The method may include visually detecting the lesion on the second surface. The method may include electrically detecting the lesion on at least one of the first surface and the second surface. Marking the second position may include applying cold to the tissue to create an ice formation that is detectable on the second surface. Applying cold to the tissue may include applying cold to the first surface and/or the second surface. The method may include visually detecting the at least one of the lesion and the ice formation on the second surface. The method may include mechanically detecting the ice formation on the second surface. Locating the second position may include distending the biological tissue by pushing on the first surface to form a protrusion on the second surface.

In a more detailed embodiment, the biological tissue may include a heart wall, the first surface may include an endocardial surface, and/or the second surface may include an epicardial surface. Locating the first position may include locating a sinoatrial node, an atrioventricular node, a ganglionic plexi, and/or an arrhythmogenic area.

In a more detailed embodiment, the biological tissue may include a heart wall, the first surface may include an epicardial surface, and/or the second surface may include an endocardial surface. Locating the first position may include locating a sinoatrial node, an atrioventricular node, a ganglionic plexi, and/or an arrhythmogenic area.

In a more detailed embodiment, locating the first position on the first surface of the biological tissue may include electroanatomical mapping.

It is an aspect of the present disclosure to provide a method of marking a biological tissue, including introducing a marking device into a surgical space, the marking device including an elongated shaft and an at least partially covered, distally disposed absorbent tip; exposing the tip; and/or marking the tissue by applying a marking substance from the tip to the tissue.

In a more detailed embodiment, the marking substance may include at least one of an ink, a dye, a radionuclide, a radiopaque substance, and a magnetic substance. The method may include, prior to introducing the marking device into the surgical space, loading the tip with a liquid. The liquid may include the marking substance. The tip may be pre-loaded with a dry form of the marking substance and/or loading the tip with the liquid may include hydrating the tip and the marking substance. The tip may include at least one microneedle and/or marking the tissue may include penetrating the tissue with the microneedle. The marking device may include a sheath slidably disposed on the shaft, the sheath being longitudinally movable between an extended configuration and a retracted configuration and/or exposing the tip may include withdrawing the sheath from the extended configuration to the retracted configuration. The sheath may be substantially transparent and/or the method may include, prior to exposing the tip, aligning a distal portion of the sheath with a portion of the tissue by viewing at least the portion of the tissue through the sheath. The tip may be longitudinally movable between an extended configuration and a retracted configuration and/or exposing the tip may include extending the tip from the retracted configuration to the extended configuration. The method may include reloading the tip with the marking substance by moving the tip from the extended configuration to the retracted configuration.

In a more detailed embodiment, the method may include, after introducing the marking device into the surgical space, guiding the tip to a desired location using magnetic attraction, magnetic repulsion, and/or an impedance measurement of the tissue. The method may include, before marking the tissue, stabilizing the marking device. Stabilizing the marking device may include stabilizing the marking device using suction and/or stabilizing the marking device using magnetic attraction.

It is an aspect of the present disclosure to provide a method of marking a biological tissue, including locating a position on a biological tissue; applying a patch at the position; and/or transferring a marking substance from the patch to the tissue.

In a more detailed embodiment, the marking substance may include at least one of an ink and a dye. The marking substance may include a radionuclide. The marking substance may include a radiopaque substance. The marking substance may include a magnetic substance. The patch may include a substrate configured to hold the marking substance. The substrate may be constructed from a bioabsorbable material and/or the method may include leaving the patch in position on the tissue after a surgical procedure. The substrate may be constructed from a biocompatible material and/or the method may include removing the patch from the tissue before completion of a surgical procedure. The substrate may be constructed from a biocompatible material and/or the method may include leaving the patch in position on the tissue after a surgical procedure. The method may include providing the patch in a dry state. The method may include applying the patch in the dry state. The method may include, before applying the patch, hydrating the patch. The patch may include the substrate and a dry form of the marking substance and/or hydrating the patch may include hydrating the marking substance. Hydrating the patch may include hydrating the patch with a liquid form of the marking substance.

It is an aspect of the present disclosure to provide a surgical device for marking a biological tissue, including an elongated shaft; a tip disposed distally on the elongated shaft, the tip comprising an absorbent material; and/or a sheath slidably disposed on the shaft, the sheath being longitudinally movable between an extended configuration and a retracted configuration. In the extended configuration, the sheath may at least partially cover a distal portion of the shaft and the tip. In the retracted configuration, at least a portion of the tip may be exposed.

In a more detailed embodiment, at least a portion of the sheath may be substantially transparent. The tip may include at least one microneedle arranged to penetrate a target tissue. The tip may be configured to be loaded with a marking substance. The tip may be loaded with the marking substance. The marking substance may include at least one of an ink and a dye. The marking substance may include a radionuclide. The marking substance may include a radiopaque substance. The marking substance may include a magnetic substance. The marking substance may be a liquid. The marking substance may be in a dry state and/or the tip and the marking substance may be configured to be hydrated prior to use.

It is an aspect of the present disclosure to provide a surgical device for marking a biological tissue, including an elongated shaft with a distally disposed tip, the tip comprising an absorbent material. The tip may be longitudinally movable between a retracted configuration and an extended configuration. In the retracted configuration, the tip may be positioned substantially within the shaft. In the extended configuration, at least a portion of the tip may be exposed.

In a more detailed embodiment, the tip may be configured to be loaded with a marking substance. The tip may be loaded with the marking substance. The marking substance may include at least one of an ink and a dye. The marking substance may include a radionuclide. The marking substance may include a radiopaque substance. The marking substance may include a magnetic substance. The marking substance may be a liquid. The marking substance may be in a dry state and/or the tip and the marking substance may be configured to be hydrated prior to use.

It is an aspect of the present disclosure to provide a patch for marking a biological tissue, including a substrate and/or a marking substance loaded in the substrate.

In a more detailed embodiment, the substrate may be configured to transfer at least some of the marking substance to a biological tissue. The marking substance may include at least one of an ink and a dye. The marking substance may include a radionuclide. The marking substance may include a radiopaque substance. The marking substance may include a magnetic substance. The substrate may be constructed from a bioabsorbable material. The substrate may be constructed from a biocompatible material. The patch may include a dry form of the substrate and a dry form of the marking substance. The patch may be configured to be placed on a biological tissue without being pre-hydrated. The patch may be configured to hydrated before being placed on a biological tissue. The marking substance may include a liquid. The substrate may include a film. The substrate may be electrically insulative.

It is an aspect of the present disclosure to provide a method of making a biological tissue marking device, including providing a substrate comprising at least one of a bioabsorbable material and a biocompatible material and/or loading a marking substance into the substrate.

In a more detailed embodiment, absorbing the marking substance into the substrate may include absorbing a liquid marking substance into the substrate. The method may include, after loading the liquid marking substance into the substrate, dehydrating the substrate and the marking substance. The method may include, prior to use, hydrating the substrate and the marking substance. Loading the marking substance into the substrate may include loading a dry form of the marking substance into the substrate. The substrate may include a film and/or providing the substrate may include forming the film.

In a more detailed embodiment, providing the substrate may include providing the substrate in a ready-to-use size and shape. Providing the substrate may include providing the substrate in a size larger than a desired use size and shape. The method may include cutting the substrate to the desired use size and shape.

BRIEF DESCRIPTION OF THE DRAWINGS

Example embodiments are described in conjunction with the accompanying drawing figures in which:

FIG. 12 is a side view of an example marking instrument in a retracted configuration;

FIG. 13 is a side view of the marking instrument in an extended configuration;

DETAILED DESCRIPTION

Figure 1:
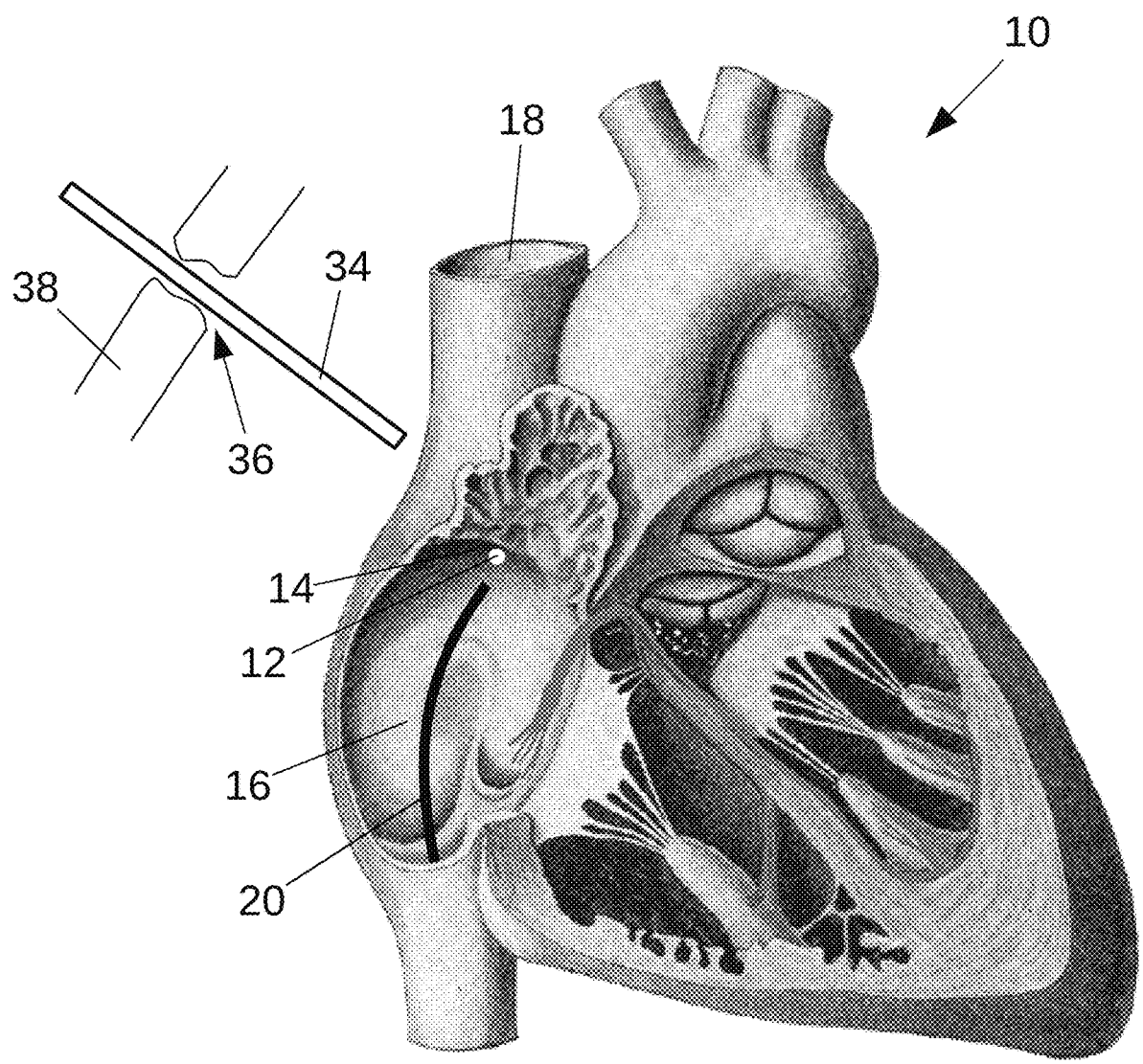
FIG. 1 is a partial cutaway view of a heart showing the approximate position of a sinoatrial node.

Example embodiments according to the present disclosure are described and illustrated below to encompass devices, methods, and techniques relating to medical and surgical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure contemplates that some surgical procedures may involve biological tissues that are accessible both from a first side and from a generally opposed second side. For example, during some hybrid cardiac procedures, both the interior surface of the heart wall (e.g., the endocardium) and the exterior surface of the heart wall (e.g., the epicardium) may be accessible. During some procedures, it may be advantageous to locate a particular position on the tissue from the first side and to perform a therapeutic procedure (e.g., ablation) from the second side. As used herein, "a position" may be a specific place or spot, such as a point, a line, a two-dimensional area, and/or a three-dimensional volume. As used herein, "to locate" may refer to an act of determining, finding, and/or identifying a position. Generally, the present disclosure includes devices for locating and/or marking positions on biological tissues, such as the wall of the heart, and related methods.

Some example embodiments according to at least some aspects of the present disclosure may be used in connection with locating a position on a second side of a biological tissue (e.g., the epicardium) corresponding to and/or utilizing a position initially located on a first side of the tissue (e.g., the endocardium). For example, during a hybrid cardiac procedure, a cardiac electrophysiologist ("EP") may locate the position of a particular anatomical structure based electrophysiological mapping performed on the endocardium (e.g., the interior surface of the heart wall). Then, a surgeon may locate and/or mark a corresponding position on the epicardium (e.g., the exterior surface of the heart wall), such as to guide acute therapy, staged therapy, and/or chronic postoperative follow-up therapy or diagnostics. For example, placement of one or more fiducial markers may facilitate future imaging studies, such as to confirm of the stability of a left atrial appendage occlusion clip applied during a hybrid left atrial appendage treatment.

Particularly when a therapeutic procedure must be performed in a specific manner to include or avoid a certain portion of the tissue, it may be advantageous to locate and/or mark a position on the second side of the tissue that corresponds to the position initially located on the first side of the tissue. For example, the position of a portion of the tissue which is to be ablated may be located on the first side of the tissue, and a corresponding position may be marked on the second side of the tissue. Then, the marking may be used to help direct the ablation device at the portion of the tissue that is to be ablated. Alternatively, the position of a portion of the tissue which is not to be ablated may be located on the first side of the tissue, and a corresponding position may be marked on the second side of the tissue. Then, the marking may be used to direct the ablation device so as to avoid ablating the marked portion of the tissue. Some example markings may be durable and/or readily detectable to facilitate subsequent location of a marked position using the marking.

FIG. 1 is a partial cutaway view of a heart 10 showing the approximate position of a sinoatrial ("SA") node 12 and FIGS. 2-7 are detailed cross-sectional views of a heart wall 14 proximate the SA node 12 illustrating example operations, all according to at least some aspects of the present disclosure.

Referring to FIG. 1, the SA node 12 is found in the heart wall 14 (e.g., myocardium) of the right atrium 16, laterally to the entrance to the superior vena cava 18. The cells of the SA node 12 produce electrical impulses that cause the heart 10 to contract. An example hybrid cardiac procedure may include treatment for an arrythmia, such as inappropriate sinus tachycardia ("IST"), which may be caused by abnormal anatomy or physiology within the heart's conduction system. Such a procedure may include epicardial ablation in the vicinity of the SA node 12; however, the position of the SA node 12 may not be readily visually apparent when viewing the epicardial surface.

Figure 2:
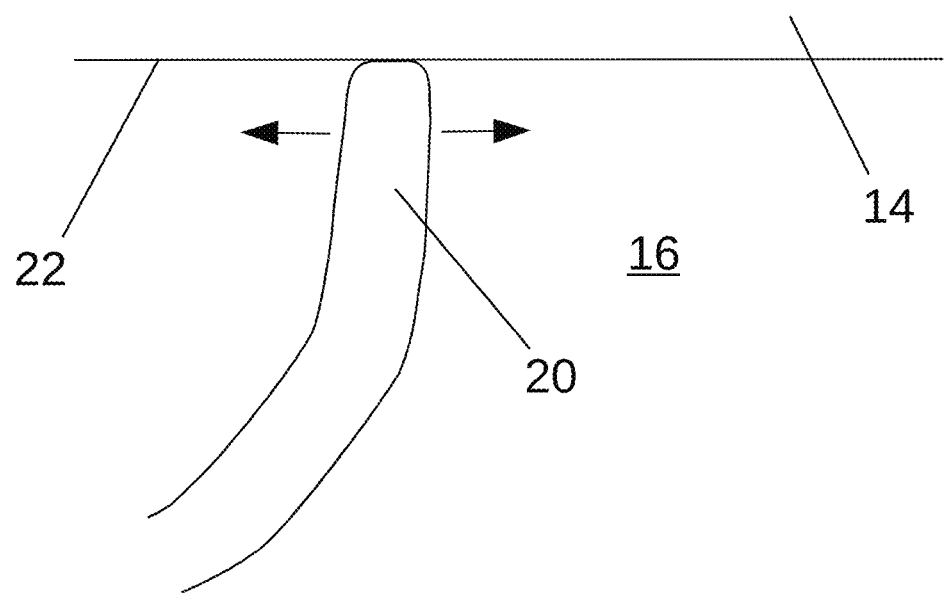
FIGS. 2-7 are detailed cross-sectional views of a heart wall proximate the sinoatrial node.
Figure 3:
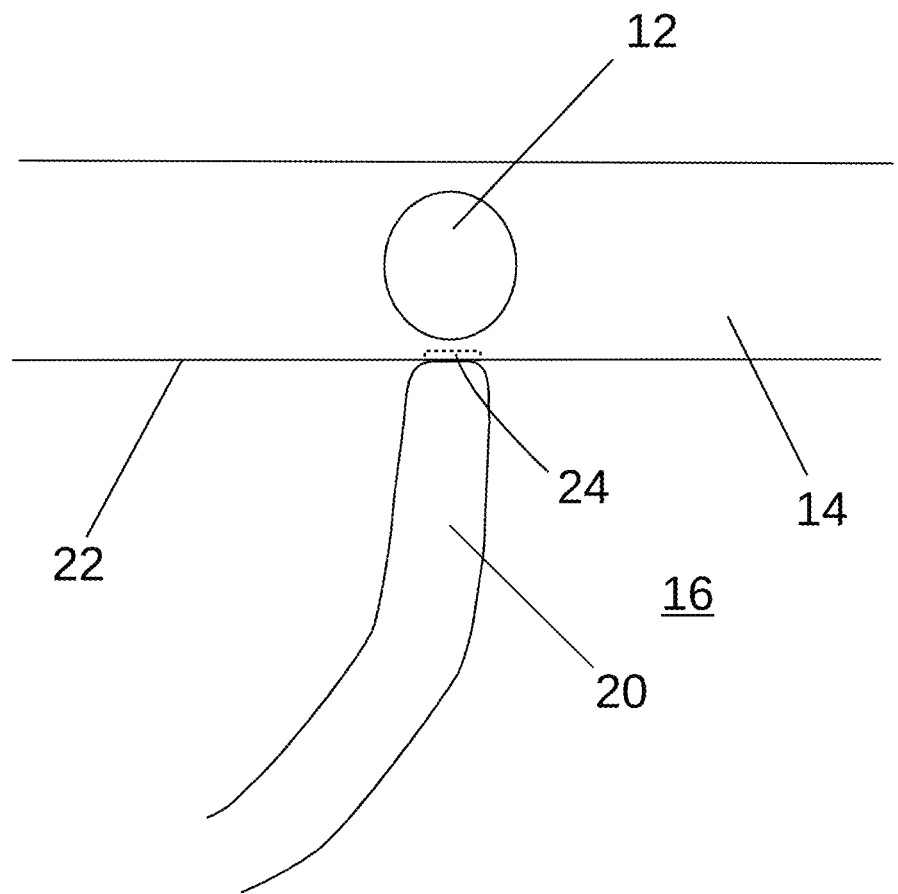

Referring to FIGS. 1-3, a physician (e.g., an EP) may use an electrical mapping catheter 20 extending within the heart 10 (e.g., within the right atrium 16) to locate a first position 24, such as a position associated with the patient's SA node 12, on a first, endocardial side 22 of the heart wall 14. For example, the EP may use known electrophysiological/electroanatomical mapping techniques to locate the position 24 of the SA node 12 on the endocardium 22. In other example embodiments, other portions of the heart wall 14 may be located, such as positions associated with an atrioventricular node, a ganglionic plexi, and/or an arrhythmogenic area.

Figure 4:
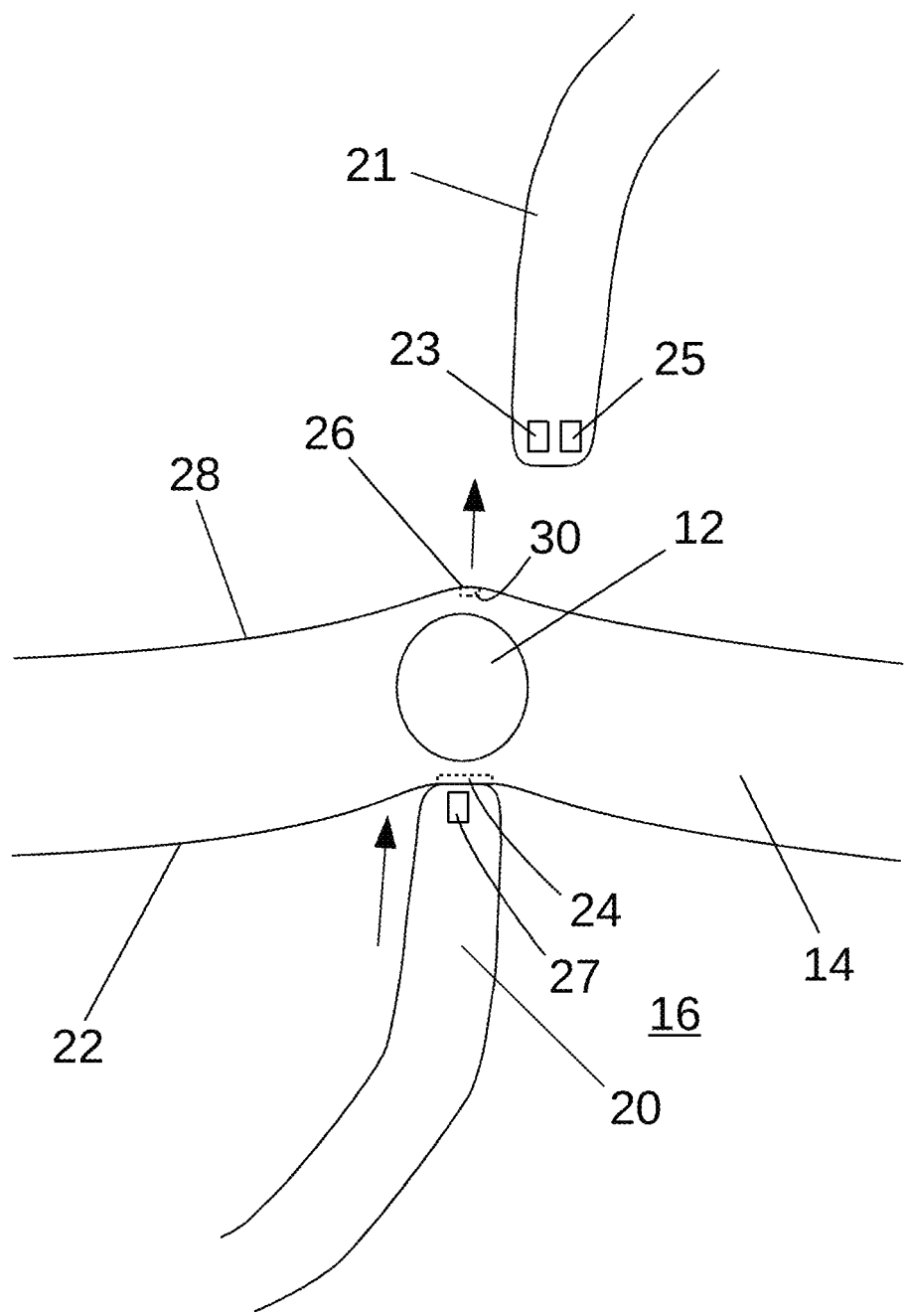

Referring to FIG. 4, the EP may distend the heart wall 14 generally outward by pushing on the endocardium 22 using the mapping catheter 20, forming a protrusion 26 on the second, epicardial surface 28. The protrusion 26 may be visible (e.g., directly or using an instrument such as an endoscope) and/or mechanically detectable (e.g., palpable directly or using an instrument) on the epicardial side 28 of the heart wall 14, thereby indicating the corresponding second position 30 on the epicardium 28. It will be appreciated that any technique for correlating the first position 24 on the endocardial surface 22 with the second position 30 on the epicardial surface 28 may be used, including the alternative techniques described elsewhere herein.

In some alternative example embodiments, the second position 30 may be located electrically, such as by using an epicardially positioned instrument 21 including a sensor 23. For example, similar to a proximity sensor, an instrument may be configured for sensing and interpreting signal amplitudes between the surfaces. For example, instrument 21 may emit an electromagnetic signal (e.g., a field or beam of electromagnetic radiation) on the second surface and sensor 23 may look for a changes in the return signal influenced by an instrument on the first surface (e.g., catheter 20) in order to correlate the tissue position between the two instruments. In other example embodiments, the instrument 21 and catheter 20 may be configured to assess changes in tissue impedance across the tissue area between two opposing poles. For example, an instrument on the second surface (e.g., instrument 21) and an instrument on the first surface (e.g., catheter 20) may be used as a closed-loop system to detect tissue impedance therebetween. Instrument 21 and catheter 20 may be aligned on their respective tissue surfaces and translated across the tissue area to assess changes in impedance, which may correlate to structures or areas of therapeutic interest in the tissue. For example, a second position 30 indicated by non-focal tissue structure (e.g., SA node) may be located by detecting a change of impedance of the tissue in that region (in relation to the surrounding tissue) between the poles of instrument 21 and catheter 20. It will be appreciated that in alternative example embodiments, similar electrical location of the second position 30 may be conducted with alternative arrangements of the instruments and/or sensors. For example, the elements positioned adjacent the first surface and the second surface may be reversed.

In some alternative example embodiments, the second position 30 may be located magnetically. For example, the sensor 23 of the epicardially positioned instrument 21 may be configured to detect one or more endocardially positioned magnets (e.g., magnets associated with the mapping catheter 20). In other example embodiments, one or more magnets 25 in the epicardially positioned instrument 21 may be configured to magnetically interact with (e.g., attract) one or more magnets 27 associated with the mapping catheter 20.

Figure 5:
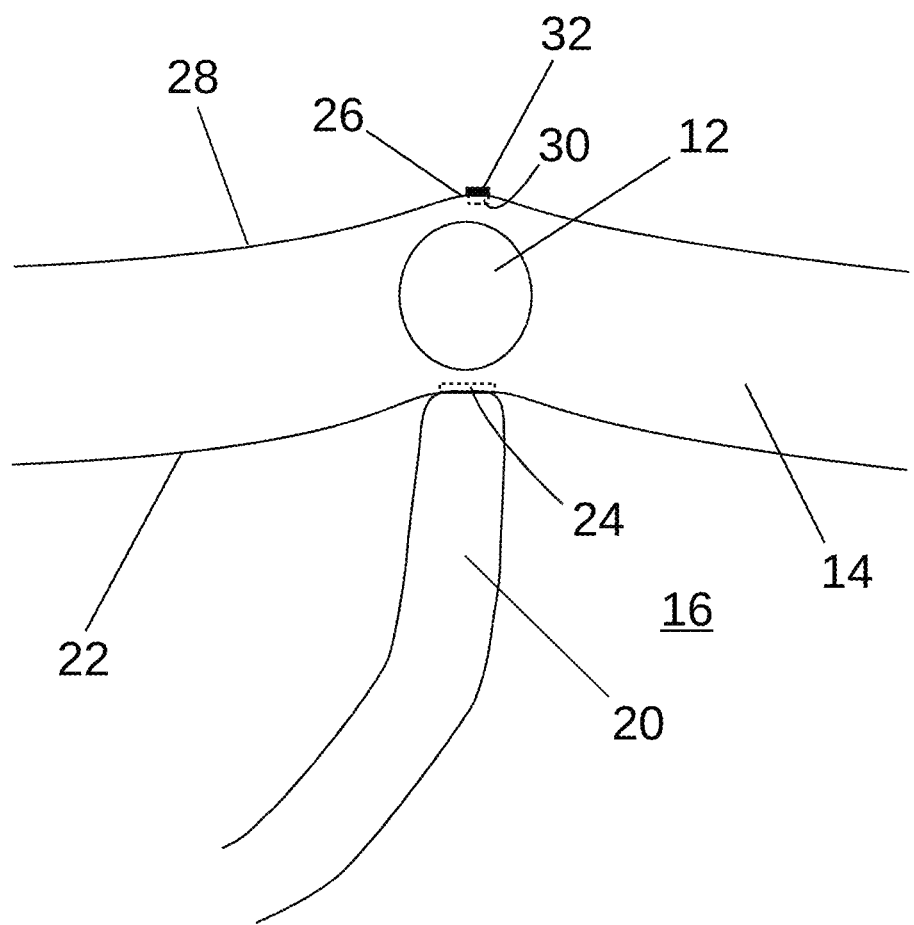

Referring to FIG. 5, the same or another physician (e.g., a cardiac surgeon) may mark the second position 30 on the epicardial side 28 of the heart wall 14, such as by disposing a marker 32 on the epicardial surface 28 at the second position 30, which may be indicated by the protrusion 26. It will be appreciated that any marking device and/or marking technique, such as those described elsewhere herein, may be utilized to facilitate marking the second position 30 with the marker 32. Generally, as used herein, "marker" may refer to an indicator of a position. A marker may include, for example, a marking substance (e.g., permanent or semi-permanent ink or dye, bioabsorbable/dissolvable patch, permanent fiducial marker which may or may not be radio-opaque) applied to a particular portion of a surface, an object placed on the surface, and/or a tissue lesion. In some example procedures, a physician may perform epicardial electrical mapping, such as before and/or after disposing the marker 32 on the epicardial surface 28.

Figure 6:
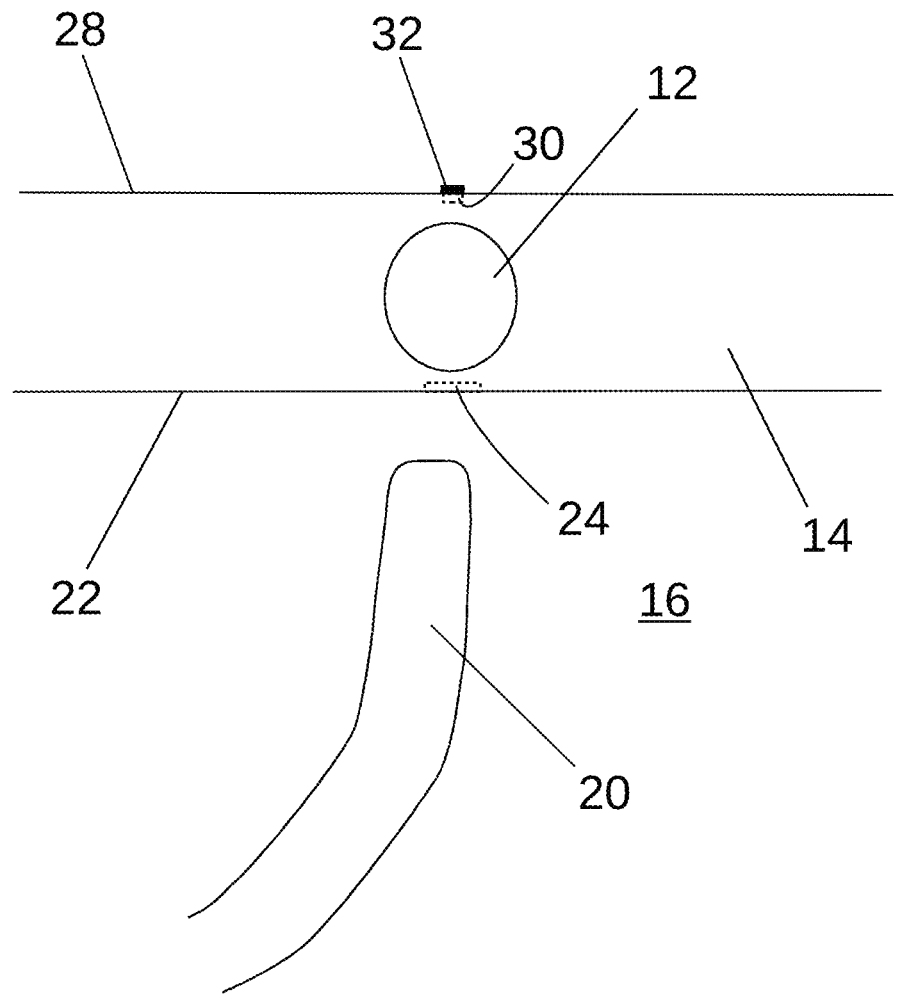

Referring to FIG. 6, the mapping catheter 20 may be at least partially withdrawn, which may remove the protrusion 26. The marker 32 may remain visible or otherwise detectable on the epicardial surface 28 at the second position 30.

Figure 7:
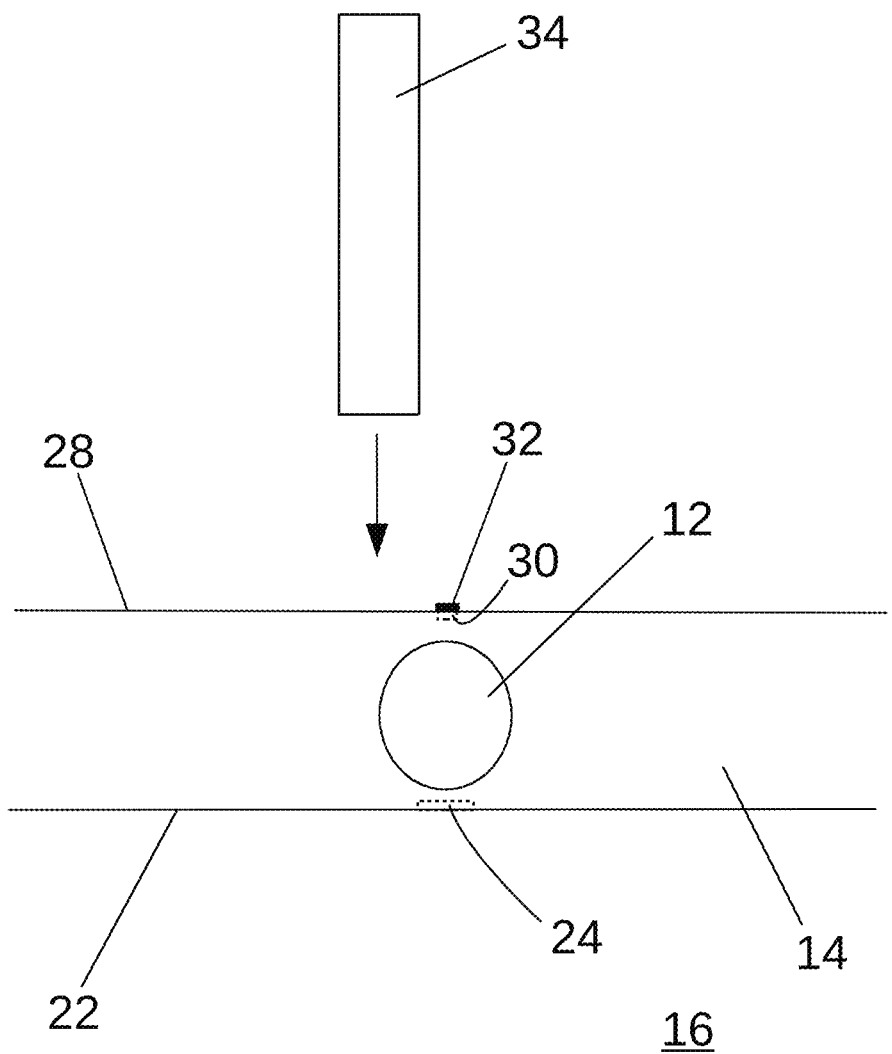

Referring to FIGS. 1 and 7, the surgeon may perform a therapeutic procedure, such as ablating portions of the heart wall proximate the SA node 12, from the epicardial 28 side of the heart wall 14. The surgeon may access the epicardium 28 via an incision 36 through the skin 38. The surgeon may utilize the marker 32 to direct a treatment device, such as an ablation device 34, to ablate the desired portions of the heart wall 14. In some procedures for treating IST, it may be desirable to ablate a portion of the heart wall 14 in the vicinity of, but not including, the portion of the heart wall 14 comprising the SA node 12. Accordingly, the surgeon may direct the ablation device 34 so that it ablates the heart wall 14 near the marker 32, while avoiding the portion of the heart wall marked by the marker 32. Alternatively, such as in other procedures or if it is necessary to ablate the SA node 12, the surgeon may direct the ablation device 34 so that it ablates a portion of the heart wall marked by the marker 32. Some example embodiments may be used in connection with longer-term follow-up procedures or diagnostics. For example, future procedures facilitated by a marker 32 may be surgical, endocardial/interventional, and/or radiotherapeutic in nature.

Although the foregoing description focused on the location and marking of positions associated with the SA node, it will be appreciated that alternative embodiments according to at least some aspects of the present disclosure, which may include similar devices and/or operations, may be utilized in connection with procedures involving other portions of the heart and/or other biological tissues. Also, although the foregoing description focused on marking a second position on a relatively outer surface (e.g., epicardium) based on a first location on a relatively inner surface (e.g., endocardium), it will be appreciated that various alternative example embodiments according to at least some aspects of the present disclosure may be utilized to mark a second position on a relatively inner surface (e.g., endocardium) based on a first location on a relatively outer surface (e.g., epicardium) using substantially similar instruments and techniques.

Figures 8, 9:
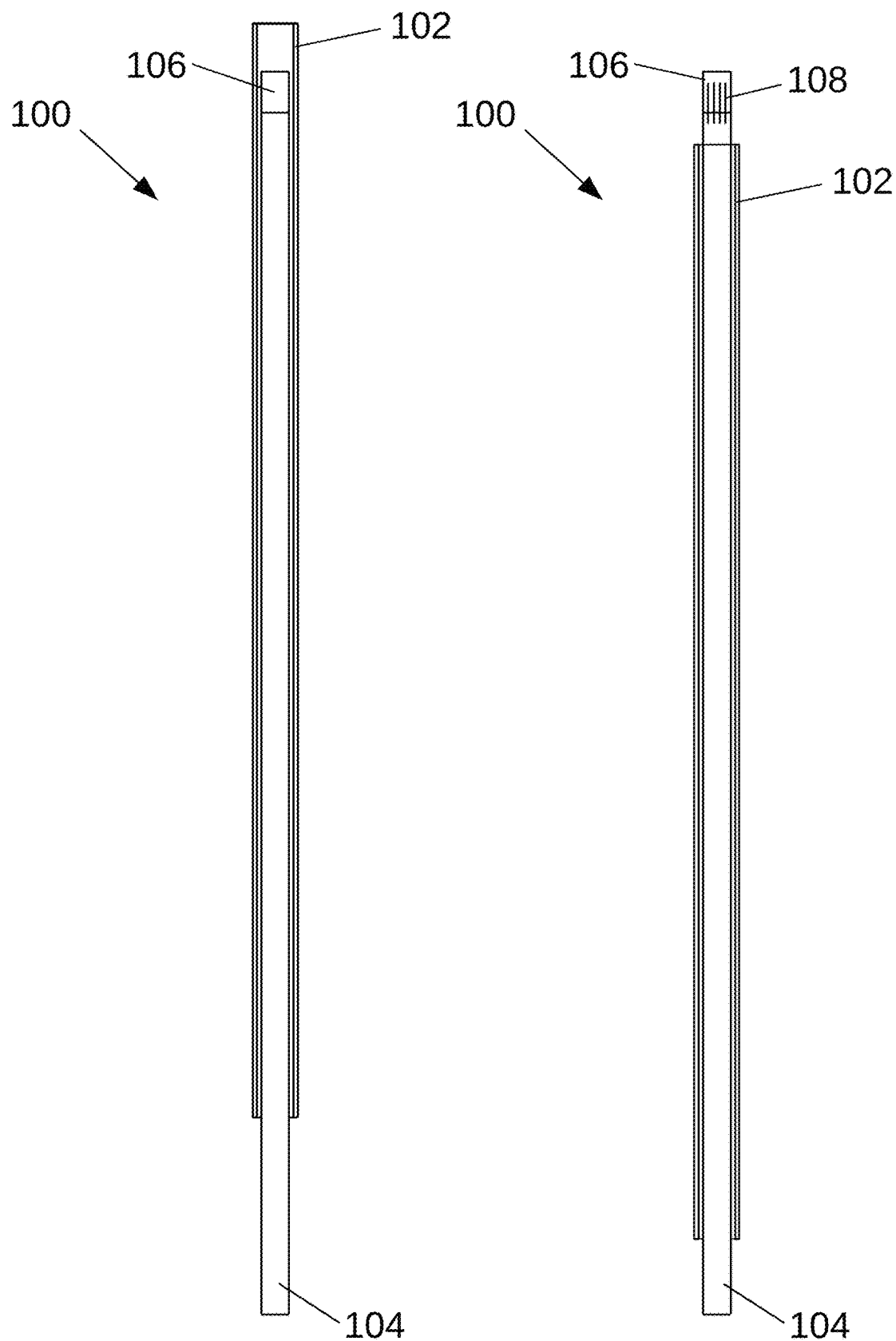
FIG. 8 is a cutaway view of an example sheathed kittner with a sheath in an extended configuration.
FIG. 9 is a cutaway view of the sheathed kittner with the sheath in a retracted configuration.

FIG. 8 is a cutaway view of an example sheathed kittner 100 with a sheath 102 in an extended configuration and FIG. 9 is a cutaway view of the sheathed kittner 100 with the sheath 102 in a retracted configuration, according to at least some aspects of the present disclosure. Generally, the illustrative sheathed kittner 100, an example marking device, includes an elongated shaft 104 with an absorbent tip 106 disposed distally thereon. The tip 106 may comprise an absorbent fabric, for example. A sheath 102 is disposed around the shaft 104 and is longitudinally movable (e.g., slidable) between an extended configuration (FIG. 8) and a retracted configuration (FIG. 9). In the extended configuration, the sheath 102 at least partially covers the distal portion of the shaft 104 and the tip 106. In the retracted configuration, at least a portion of the tip 106 is exposed and is arranged to contact the tissue that is intended to be marked (the "target tissue").

Generally, the sheath 102 may be configured so that, in the extended configuration, the sheath 102 prevents the tip 106 from contacting tissues or surfaces other than the target tissue. For example, a distal portion of the sheath 102 may extend distally beyond the tip 106. In some example embodiments, at least a portion of the sheath 102 may be substantially transparent. This may allow the user to visualize the relative position of the endoscopic kittner 100 in relation to the target tissue. The sheath may also contain features such as an insufflation seal to prevent loss of pressure from the chest cavity during the procedure, visible depth index markers (radiopaque or otherwise), a friction feature to hold the sheath in a relative position to the kittner, or a handle, among others.

The absorbent tip 106 may be dipped in or otherwise loaded with a liquid marking substance (e.g., ink or dye, radiopaque contrast media) for marking tissue. For example, the kittner 100 may be supplied with the tip 106 pre-wetted with the marking substance. In other embodiments, the tip 106 may be pre-loaded with a dry marking substance, which may be hydrated at the time of use. In other embodiments, a cartridge containing a liquid marking substance may be supplied with the kittner 100, and the tip 106 may be loaded with the marking substance at the time of use. In some example embodiments, the sheath 102 may serve as an ink well for the marking substance loaded kittner as the marking substance is wicked up the sheath. By drawing the tip 106 back into the sheath 102, the tip 106 may be at least partially reloaded with the marking substance. Generally, the tip 106 may be configured to carry sufficient marking substance to allow the user to create small "point" marks and/or to create more complex shapes on the target tissue as desired.

Generally, the sheathed kittner 100 may be prepared for use, such as by loading the tip 106 with marking substance and/or placing the sheath 102 in the extended configuration (FIG. 8). The sheathed kittner 100 may be introduced into the surgical space, such as through a minimally invasive surgical access device (e.g., a sheath or trocar) or directly through a skin incision. Once in the surgical space, the sheath 102 may be advanced to the target tissue and aligned to direct the marking substance from the tip 106 at a desired position on the target tissue. The user may press and hold the sheath 102 against the target tissue. The sheath 102 may be withdrawn to the retracted configuration (FIG. 9), exposing the tip 106, and the tip 106 may be used to mark the target tissue by applying the marking substance (e.g., ink) to the target tissue. The sheath 102 may be returned to the extended configuration (FIG. 8), and the sheathed kittner 100 may be withdrawn from the surgical field.

The sheathed kittner 100 in FIG. 9 includes optional microneedles 108, which may be configured to at least partially penetrate the target tissue, which may facilitate application of the marking substance below the surface of the target tissue in a manner similar to a tattoo.

Figure 10:
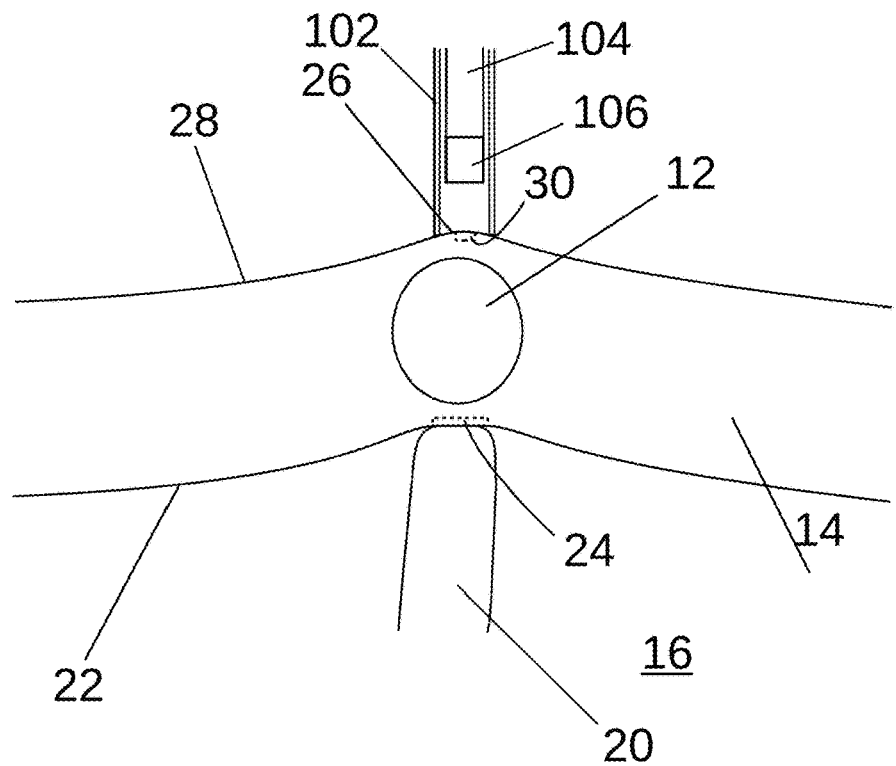
FIGS. 10 and 11 are cross-sectional views illustrating an example method of using a sheathed kittner to mark the epicardium.
Figure 11:
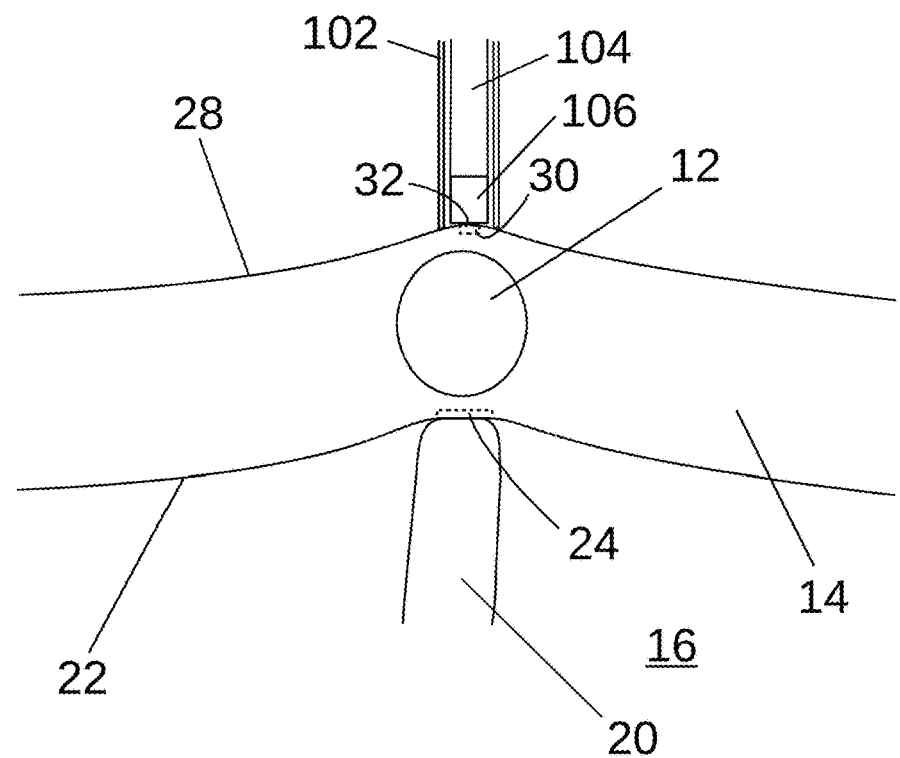

FIGS. 10 and 11 are cross-sectional views illustrating an example method of using a sheathed kittner 100 to mark the epicardium 28, according to at least some aspects of the present disclosure. In this example, the sheathed kittner 100 is used to apply the marker 32 at the second position 30 associated with the SA node 12 as described above in connection with FIGS. 2-7. Referring to FIG. 10, the sheathed kittner 100, with the sheath 102 in the extended configuration, may be advanced to align the distal portion of the sheath 102 with the protrusion 26 indicating the second position 30, which may comprise the target tissue. Then, the shaft 104 may be moved distally relative to the sheath 102 to cause the tip 106 to contact the second surface (e.g., epicardium) 28 at the second position 30, disposing the marker 32 comprising the marking substance (e.g., ink) from the tip 106 thereon as shown in FIG. 11.

It will be appreciated that various illustrative sheathed kittners 100 according to the present disclosure may be used to mark positions, such as the second position 30, in any desired size or shape. A sheathed kittner 100 may be used to mark a point, a line, and/or a two-dimensional area, for example.

FIG. 12 is a side view of an example marking instrument 200 in a retracted configuration and FIG. 13 is a side view of the marking instrument 200 in an extended configuration, according to at least some aspects of the present disclosure. Generally, the illustrative marking instrument 200, an example marking device, includes an elongated shaft 202 with a distally disposed tip 204. The tip 204 may comprise an absorbent fabric, for example. The tip 204 may be longitudinally movable (e.g., slidable) between the retracted configuration (FIG. 12) and the extended configuration (FIG. 13). Positioning of the movable component may be controlled by a spring-loaded button 206, which may be disposed proximally, such as on a handle 208. Extension limit of the moving component may be achieved with detents on the button component 206 which mate with the handle component 208. In the retracted configuration, the tip 204 is positioned substantially within the shaft 202 so that the tip 204 does not mark adjacent tissues. In the extended configuration, at least a portion of the tip 204 is exposed (e.g., extends distally beyond the shaft 202) and is arranged to contact the target tissue. In some example embodiments, suction may be applied down the lumen of the device to assist with keeping the instrument in place during use.

The tip 204 may be dipped in or otherwise loaded with a liquid marking substance (e.g., ink or dye) for marking tissue. For example, the marking instrument 200 may be supplied with the tip 204 pre-wetted with the marking substance. In other embodiments, the tip 204 may be pre-loaded with a dry marking substance, which may be hydrated at the time of use. In other embodiments, a cartridge containing liquid marking substance may be supplied with the marking instrument 200, and the tip 204 may be loaded with the marking substance at the time of use. Generally, the tip 204 may be configured to carry sufficient marking substance to allow the user to create small "point" marks or to create more complex shapes on the target tissue as desired.

Generally, the marking instrument 200 may be prepared for use, such as by loading the tip 204 with the marking substance and/or placing the tip 104 in the retracted configuration (FIG. 12). The marking instrument 200 may be introduced into the surgical space, such as through a minimally invasive surgical access device (e.g., a sheath or trocar) or directly through a skin incision. Once in the surgical space, the shaft 202 may be advanced to the target tissue and aligned to direct the marking substance from the tip 204 at a desired position on the target tissue. The tip 204 may be extended (FIG. 13), and the tip 204 may be used to mark the target tissue by applying the marking substance to the target tissue. The tip 204 may be returned to the retracted configuration (FIG. 12), and the marking instrument 200 may be withdrawn from the surgical field.

In some example embodiments, a marking device, such as a marking instrument 200, may include one or more features configured to facilitate guiding the tip 204 to the desired location. For example, referring to FIG. 12, the marking instrument 200 may include one or more sensors, such as an impedance sensor 210, which may be configured to sense the impedance of the target tissue. As another example, the marking instrument 200 may include one or more magnets 212, which may be attracted or repelled by a corresponding magnet associated with another instrument, such as a magnet 27 of a mapping catheter 20 (FIG. 4). Accordingly, after the marking instrument 200 has been introduced into the surgical space, the tip 204 may be guided to a desired location using magnetic attraction, magnetic repulsion, and one or more impedance measurements of the tissue. It will be appreciated that similar guidance may be utilized in connection other example marking devices, such as the sheathed kittner described above.

In some example embodiments, a marking device, such as a marking instrument 200, may include one or more features configured to facilitate stabilizing the marking instrument 200. For example, referring to FIG. 13, the marking instrument 200 may include a distal suction opening 214 operatively connected to a suction source 216 via a suction tube 218. Application of suction may temporarily secure the distal suction opening 214 to the tissue, thereby stabilizing the marking instrument 200. As another example, the magnet 212 may be configured to be attracted to a corresponding magnet associated with another instrument, such as a magnet 27 of a mapping catheter 20 (FIG. 4), thereby stabilizing the marking instrument 200. Accordingly, before marking the tissue, the marking instrument 200 may be stabilized, such as by using suction and/or using magnetic attraction. It will be appreciated that similar stabilization may be utilized in connection other example marking devices, such as the sheathed kittner described above.

Figure 14:
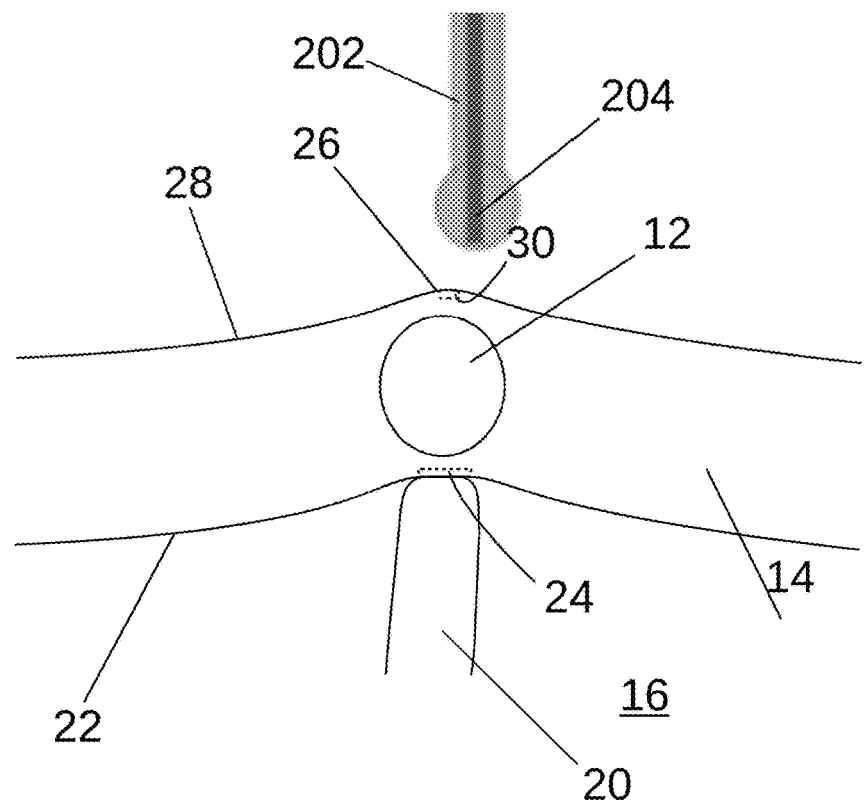
FIGS. 14 and 15 are partial cross-sectional views illustrating an example method of using a marking instrument to mark the epicardium.
Figure 15:
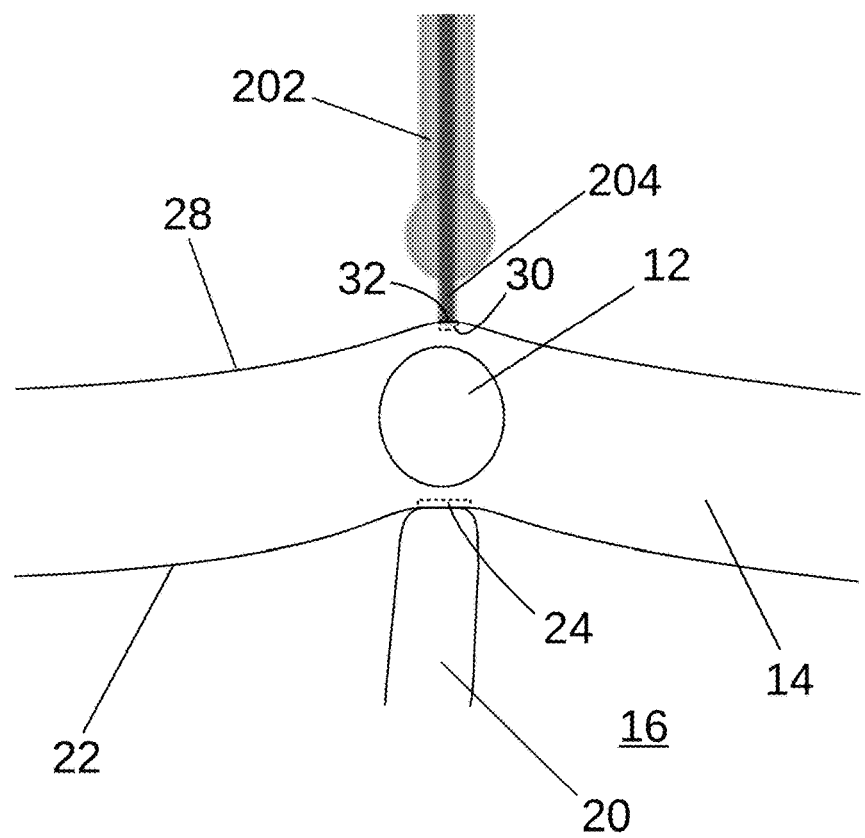

FIGS. 14 and 15 are partial cross-sectional views illustrating an example method of using a marking instrument 200 to mark the epicardium 28, according to at least some aspects of the present disclosure. In this example, the marking instrument 200 is used to apply a marker 32 at the second position 30 associated with the SA node 12 as described above in connection with FIGS. 2-7. Referring to FIG. 14, the marking instrument 200, with the tip 204 in the retracted configuration, may be advanced into the surgical space near the protrusion 26 indicating the second position 30, which may comprise the target tissue. The tip 204 may be placed into the extended configuration. Referring to FIG. 15, the shaft 202 may be manipulated to cause the tip 204 to contact the second surface (e.g., epicardium) 28 at the second position 30, disposing the marker 32 comprising the marking substance from the tip 204 thereon.

It will be appreciated that various illustrative marking instruments 200 according to the present disclosure may be used to mark positions, such as the second position 30, in any desired size or shape. A marking instrument 200 may be used to mark a point, a line, and/or a two-dimensional area, for example.

Figure 16:
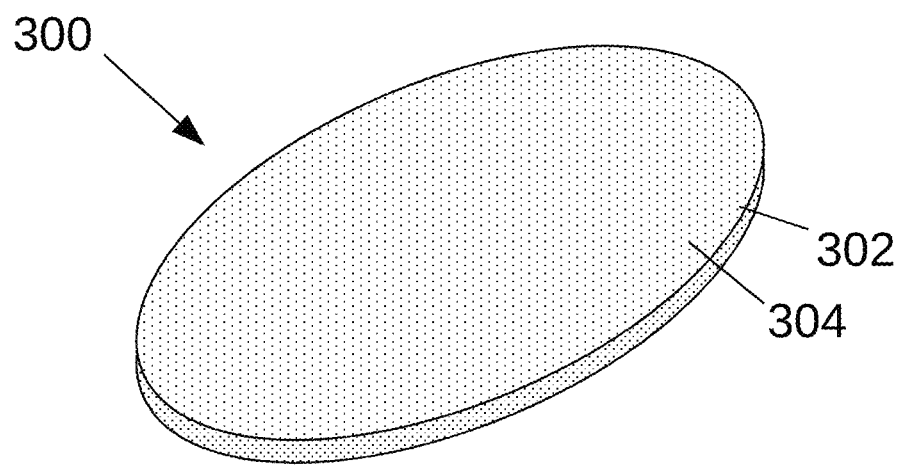
FIG. 16 is an isometric view of an example patch.

FIG. 16 is an isometric view of an example patch 300, according to at least some aspects of the present disclosure. Generally, the illustrative patch 300 is an object that can be placed on a biological tissue to mark a position. The patch 300 may be constructed of a substrate 302. The patch 300 may comprise the marker 32 mentioned elsewhere herein.

In some example embodiments, the substrate 302 may be constructed of one or more bioabsorbable materials. Such substrates 302 may be constructed from, for example, oxidized regenerated cellulose (ORC), polyglycolic acid (PGA) felt, collagen sponge (which may be coated with fibrinogen and/or thrombin), monofilament mesh (e.g., poly-4-hydroxybutyrate (P4HB)), and/or a biosynthetic web scaffold (e.g., polyglycolic acid (PGA) and trimethylene carbonate (TMC)). Some example bioabsorbable substrates 302 may be radiopaque or may be doped to be radiopaque. In some example embodiments, the substrate 302 may comprise a film, which may be made by molding gelatin or oxidized regenerated cellulose, for example. Some patches 300, such as patches 300 comprising substrates 302 constructed of bioabsorbable materials, may be placed on the biological tissue during a procedure and/or may be left in position on the tissue after the procedure. Some such patches 300 may be absorbed by the body over time. Alternatively, patches 300 may be removed from the biological tissue before the end of the procedure.

In some example embodiments, the substrate 302 may be constructed of non-bioabsorbable materials. Some such substrates 302 may be constructed from biocompatible materials, for example, polyester, polyurethane, silicone, or a polyolefin (e.g., polypropylene or polyethylene). Some example non-bioabsorbable substrates 302 may be radiopaque or may be doped to be radiopaque. Some patches 300, such as patches 300 comprising substrates 302 constructed of non-bioabsorbable materials, may be placed on the biological tissue during a procedure and/or may be removed from the biological tissue before the end of the procedure. Alternatively, patches 300 may be left in position on the tissue after the procedure. These forms may or may not initiate fibrotic infiltration for long term stability.

In some example embodiments, a patch 300 may perform a function in connection with a treatment procedure. For example, a patch 300 comprising a substrate 302 that is electrically insulative may be used in connection with an ablation procedure. The patch 300 may electrically insulate at least some of the underlying tissue from the by disrupting the electrical ablation signal. For example, electrical isolation may be achieved by incorporating coatings such as polyamideimide (reference Elantas PDG Elan-Film Insulation Sheet) or electrical grade polyester (reference Von Roll DMD-100 White Triplex Flexible Laminate Sheet) or incorporation of insulative materials such as polyimide into the formulation of the patch (reference DuPont Kapton HPP Low Shrinkage Polyimide Film Sheet Catalog). Accordingly, such a patch 300 may act as a protective patch for a portion of the underlying tissue, such as to prevent accidental ablation via the electrically insulative properties of the patch.

In some example embodiments, the patch 300 may be provided in a dry state. The patch 300 may be hydrated before use, or it may be applied to the target tissue in a dry state. Alternatively, the patch may be provided in a hydrated state.

In some example embodiments, the patch 300 may facilitate application of a marking substance, such as an ink or dye 304, to the biological tissue to comprise the marker 32. Specifically, the substrate 302 may be used to hold dye 304 and/or facilitate applying the dye 304 to the target tissue. Generally, delivering the dye 304 using the patch 300 may allow for more consistent marker 32 creation, potentially allowing more users to perform safer surgery, and/or potentially preventing the dye 304 from spreading or rubbing off of the target tissue. In a cardiovascular surgery, applying a dye 304 using a patch 300 may improve safety for beating-heart procedures because it may reduce risk of damaging the heart with a potentially traumatic tip of a surgical marker or similar device.

In some example embodiments, the patch 300 comprising the substrate 302 may be provided separately from the dye 304. Prior to use, a liquid dye 304 or a dry dye 304 mixed with water may be absorbed into the substrate 302. Then, the patch 300 may be placed on the target tissue. At least some of the dye 304 from the patch 300 may transfer to the target tissue, thereby creating a visible marker 32 on the target tissue.

In other example embodiments, the patch 300 comprising the substrate 302 and the dye 304 may be provided in a dry state. Prior to use, the patch 300 may be wetted, such as with water. Then, the hydrated patch 300 may be placed on the target tissue. At least some of the dye 304 from the patch 300 may transfer to the target tissue, thereby creating a visible marker 32 on the target tissue.

In other example embodiments, the patch 300 comprising the substrate 302 and the dye 304 may be provided in a hydrated state. The hydrated patch 300 may be placed on the target tissue, and at least some of the dye 304 from the patch 300 may transfer to the target tissue, thereby creating a visible marker 32 on the target tissue.

In some example embodiments, patches 300 configured to apply a marking substance, such as dye 304, to the target tissue may be applied to the target tissue, left in place to allow at least some of the marking substance to transfer to or act on the target tissue, and may be removed from the target tissue.

Patches 300 may be configured to adhere to the target tissue in a hydrated and/or a dry state. Patches 300 may be formed in standard sizes and/or may be made into a specific size and/or shape based upon the target tissue and/or the patient. In some embodiments, the patch 300 may be generally in the form of a small circle or oval as shown in FIG. 16. However, the size of the dye delivery patch is not limited and may be a variety of shapes and/or sizes based upon the target tissue. For example, some patches 300 (e.g., substrate 302) may be provided in a ready-to-use size and shape. Alternatively, some patches 300 (e.g., substrate 302) may be provided in a size larger than a desired use size and/or shape. Then, a user may cut the patch 300 (e.g., substrate 302) to the desired use size and/or shape.

Some example embodiments are described herein as using various marking substances to provide a marker on a target tissue. Generally, it is within the scope of this disclosure to utilize any ink, dye, or other marking substance in connection with any embodiment described herein as using any such marking substance. For example, dyes such as methylene blue, gentian violet, Brilliant Blue FCF, and Evans Blue may be used as marking substances in various illustrative embodiments.

In some example embodiments, a marker and/or marking substance may comprise a radiopaque substance, which may facilitate detection of a marker using fluoroscopy, for example. If the marker remains in the patient's body, the marker may be visible using fluoroscopy, for example, after the surgical procedure. Various known contrast agents may be used, such as iodine, including ioversal (a compound which contains organically bound iodine) or barium sulfate compounds. In some example embodiments, a marking substance may include an ink or dye to facilitate direct or endoscopic visibility as well as a radiopaque agent to facilitate fluoroscopic detection. In other embodiments, a marking substance may include only a visible marking substance (e.g., ink or dye) or only a radiopaque marking substance. Some example embodiments may include markers and/or marking substances comprising at least one radionuclide (for example, iodine-131 or technetium-99).

Some example embodiments may include markers and/or marking substances comprising at least one magnetic substance (e.g., a ferromagnetic material). Generally, as used herein, "magnetic substance" may refer to a material that is itself magnetic or a material that is capable of being attracted to a magnet. Magnetic substances used in connection with markers and/or marking substances may be used to facilitate subsequent detection and/or location of a previously placed marker, for example. Additionally, in some example embodiments, the magnetic nature of a marker and/or marking substance comprising a magnetic substance may be utilized to facilitate application of the marking and/or marking substance at a particular position, such as by attraction of the magnetic substance on the second surface to a magnet on the first surface (e.g., magnet 27 associated with the mapping catheter 20). For example, a second position may be magnetically located by attracting a marker and/or marking substance to the second position using a magnet at the first position on the first surface.

Figure 17:
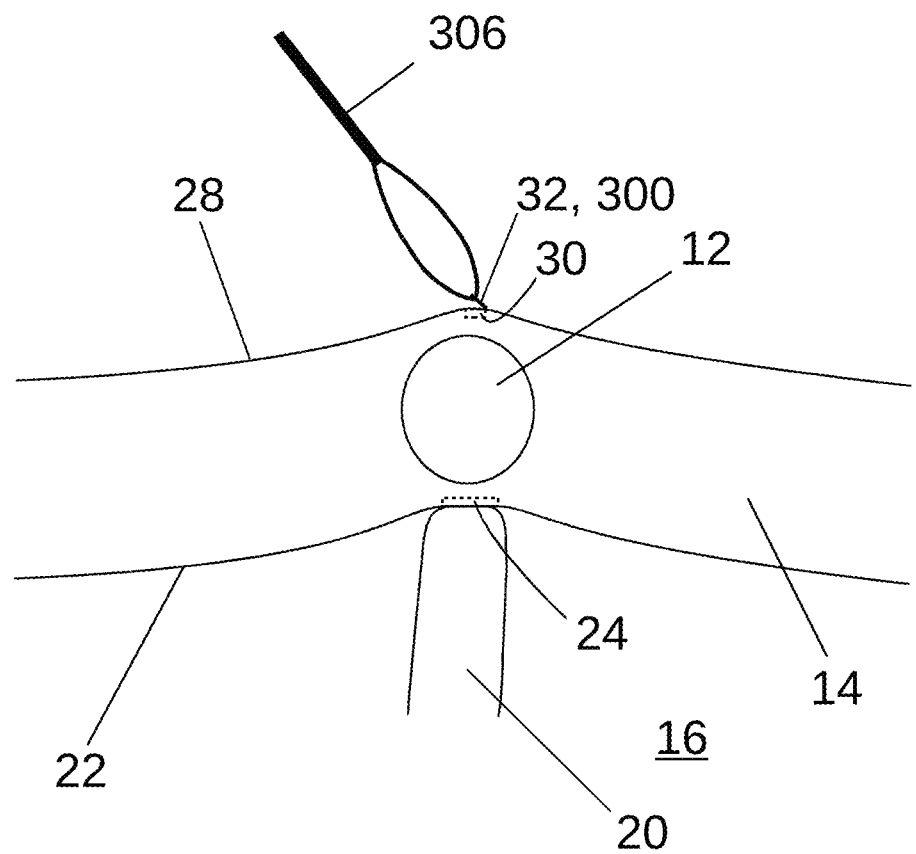
FIG. 17 is a partial cross-sectional view illustrating an example method of applying a patch.

FIG. 17 is a partial cross-sectional view illustrating an example method of applying a patch 300, according to at least some aspects of the present disclosure. In this example, the patch 300 may comprise the marker 32 that is disposed at the second position 30 associated with the SA node 12 as described above in connection with FIGS. 2-7, or the patch 300 may facilitate delivery of a marking substance that comprises the marker 32. The patch 300 may be disposed on the epicardial surface 28 using a surgical instrument, such as a grasper 306.

Figure 18:
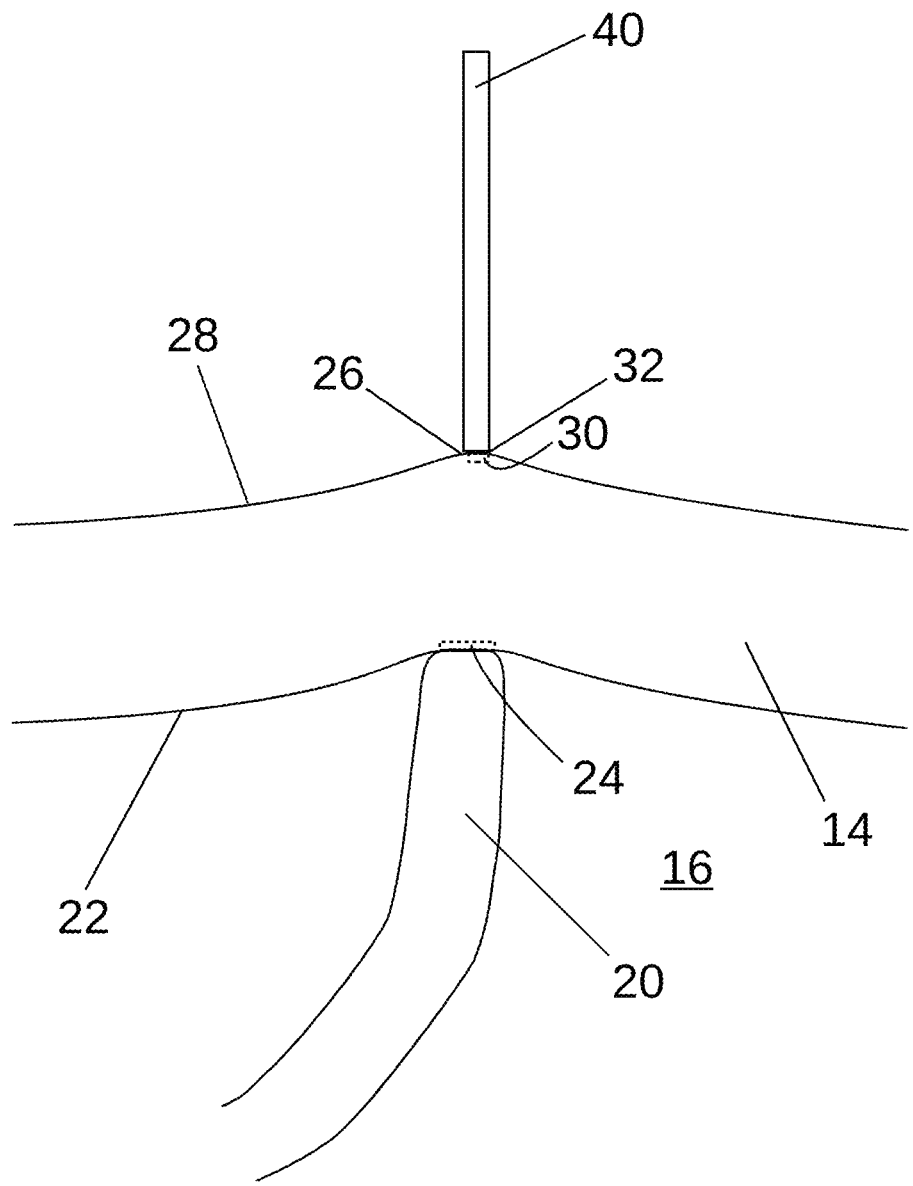
FIG. 18 is a detailed cross-sectional view of a heart wall showing an RF ablation device creating a marker comprising a lesion on the second (epicardial) surface.
Figure 19:
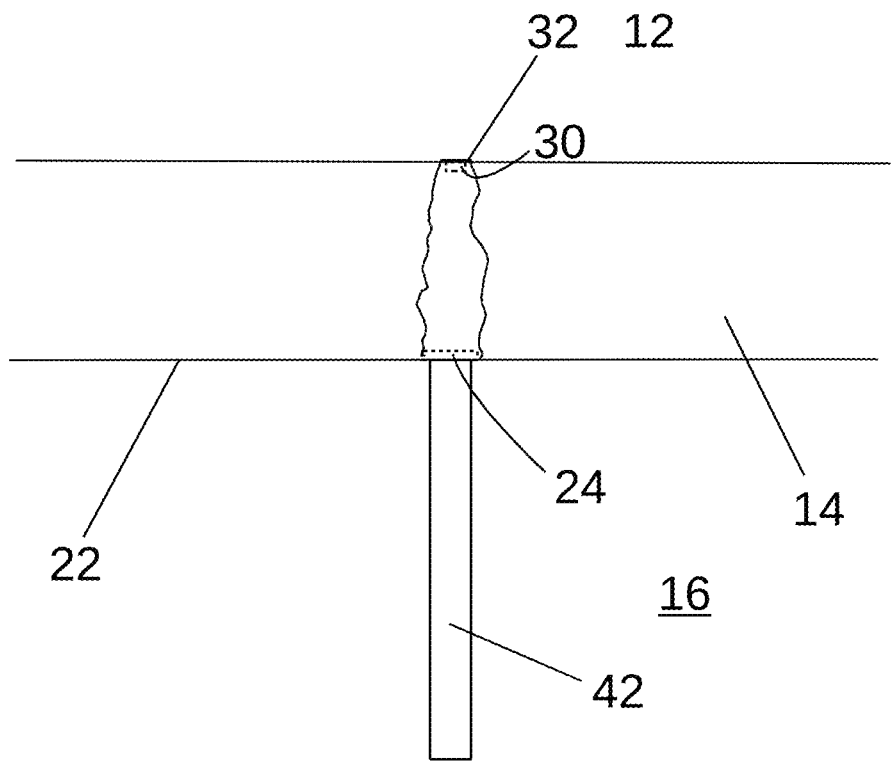
FIG. 19 is a detailed cross-sectional view of a heart wall showing a cryosurgical device creating a marker comprising ice formation visible on the second (epicardial) surface.

In some example embodiments, the marker 32 may comprise a tissue lesion, such as a lesion created by a radiofrequency ("RF") ablation device and/or a cryosurgical device. FIG. 18 is a detailed cross-sectional view of a heart wall 14 showing an RF ablation device 40 creating a marker 32 comprising a lesion on the second (epicardial) surface 28, according to at least some aspects of the present disclosure. In some example embodiments, the RF ablation may be performed at a relatively low energy level. Accordingly, the ablation may have no significant effect on the structure and/or function of the ablated tissue, other than to create the visually apparent marker 32. In some example embodiments, the lesion may heal over time. FIG. 19 is a detailed cross-sectional view of a heart wall 14 showing a cryosurgical device 42 creating a marker 32 comprising ice formation visible on the second (epicardial) surface 28, according to at least some aspects of the present disclosure. In this example embodiment, the cryosurgical device 42 applies cold to the first (endocardial) surface 22 proximate the first position 24. As the cryosurgical device 42 is cooled, the tissue freezes creating ice formation, comprising the marker 32, becomes visible on the second surface 28. In alternative example embodiments, an RF ablation 40 device may be applied to the first (endocardial) surface 22 to create a lesion visible on the second (epicardial) surface 28 and/or a cryosurgical device 42 may be applied to the second (epicardial) surface 28 to create a visually apparent ice formation.

Figure 20:
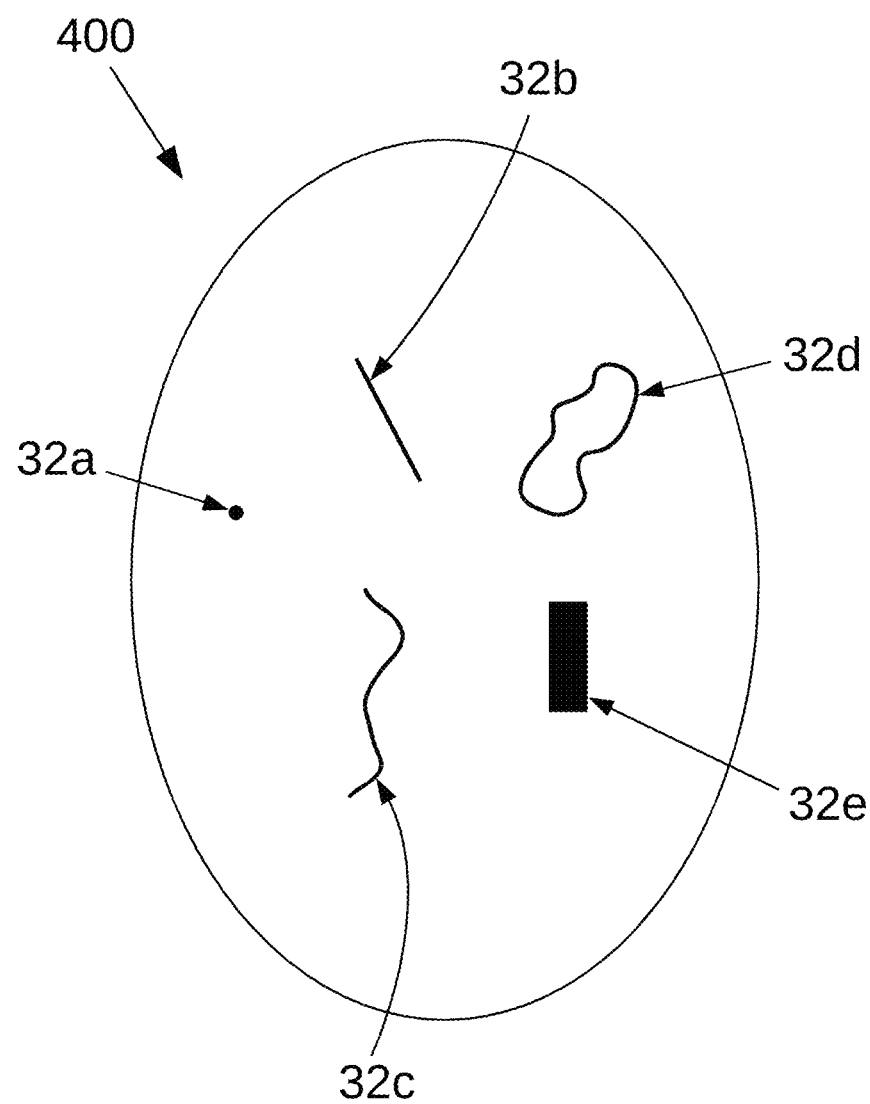
FIG. 20 is an isometric view of a biological tissue with example markers thereon; all in accordance with at least some aspects of the present disclosure.

FIG. 20 is an isometric view of a biological tissue 400 with example markers 32a, 32b, 32c, 32d, 32e thereon, according to at least some aspects of the present disclosure. Generally, the example markers 32a, 32b, 32c, 32d, 32e represent illustrative embodiments of various markers (e.g., marker 32) described herein. The markers 32a, 32b, 32c, 32d, 32e may be in the form of a marking substance (e.g., ink or dye) applied by a sheathed kittner 100 or a marking instrument 200, an object such as a patch 300, a marking substance (e.g., an ink or dye) applied by a patch 300, ice formation, and/or a tissue lesion, for example. Generally, markers described herein may be in the form of a circular or non-circular dot (e.g., point 32a), a line (e.g., straight line 32b or curved line 32c), or an area (e.g., perimeter 32d or filled area 32e), for example. As used herein, "line" may refer to a long, thin shape, and a line may be substantially straight or may include one or more curves, bends, or angles. Markers according to the present disclosure may be standardized or may be sized and/or shaped specifically for particular patients and/or applications.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Further, it is to be understood that, in general, any feature or aspect described in connection with one embodiment may be used in connection with any other embodiments. Likewise, it is to be understood that it is not necessary to meet any or all of the identified advantages or objects disclosed herein in order to fall within the scope of the claims, since inherent and/or unforeseen advantages may exist even though they may not have been explicitly discussed herein.

What is claimed is:

1. A method of performing an operation, the method comprising:
    locating a first position on a first interior surface of a heart wall responsive to an electrophysiological mapping performed on the first interior surface;
    using a surgical instrument to apply pressure to the first interior surface and create a protrusion on a second exterior surface of the heart wall without through puncturing the heart wall, the protrusion corresponding to a second position; and
    marking the second position on the second exterior surface using a location of the protrusion.

2. The method of claim 1, further comprising, after marking the second position, performing a therapeutic procedure on the biological tissue in the vicinity of the second position.

3. The method of claim 2, wherein performing the therapeutic procedure comprises ablating a portion of the biological tissue.

4. The method of claim 2, wherein performing the therapeutic procedure comprises performing the therapeutic procedure on the biological tissue near but not at the second position.

5. The method of claim 2, wherein performing the therapeutic procedure comprises performing the therapeutic procedure on the biological tissue at the second position.

6. The method of claim 1, wherein marking the second position comprises marking a point on the second surface.

7. The method of claim 1, wherein marking the second position comprises marking a line on the second surface.

8. The method of claim 1, wherein marking the second position comprises marking an area on the second surface.

9. The method of claim 8, wherein marking the area comprises marking a perimeter of the area.

10. The method of claim 9, wherein marking the area comprises marking substantially all of an internal area defined by the perimeter.

11. The method of claim 1, wherein marking the second position comprises disposing a marker on the second surface.

12. The method of claim 11, wherein the marker comprises a marking sub stance.

13. The method of claim 12, wherein the marking substance comprises at least one of an ink and a dye.

14. The method of claim 12, wherein the marking substance comprises a radionuclide.

15. The method of claim 12, wherein the marking substance comprises a radiopaque substance.

16. The method of claim 12, wherein the marking substance comprises a magnetic substance.

17. The method of claim 11, wherein the marker comprises an object.

18. The method of claim 17, wherein the object comprises a magnetic sub stance.

19. The method of claim 17,
    wherein the object is electrically insulative; and
    wherein the method further comprises applying RF energy to the tissue while at least a portion of the tissue is protected from the RF energy by the marker.

20. The method of claim 17, wherein the object is bioabsorbable.

21. The method of claim 11, wherein disposing the marker on the second surface comprises at least partially penetrating the second surface.

22. The method of claim 1, wherein marking the second position comprises heating the tissue to create a lesion that is detectable on the second surface.

23. The method of claim 22, wherein heating the tissue comprises at least one of applying RF energy, microwave energy, and laser energy.

24. The method of claim 23, further comprising visually detecting the lesion on the second surface.

25. The method of claim 24, further comprising electrically detecting the lesion on at least one of the first surface and the second surface.

26. The method of claim 1, wherein marking the second position comprises applying cold to the tissue to create an ice formation that is detectable on the second surface.

27. The method of claim 26, wherein applying cold to the tissue comprises applying cold to at least one of the first surface and the second surface.

28. The method of claim 27, further comprising visually detecting the ice formation on the second surface.

29. The method of claim 27, further comprising mechanically detecting the ice formation on the second surface.

30. The method of claim 1, wherein locating the first position comprises locating at least one of a sinoatrial node, an atrioventricular node, a ganglionic plexi, and an arrhythmogenic area.

31. A method of performing an operation, the method comprising:

locating a first position on an interior surface of a biological tissue;

using a surgical instrument to apply pressure to the interior surface and create a protrusion on an exterior surface of the biological tissue, the protrusion corresponding to a second position; and applying a patch to the second position on the exterior surface.

32. The method of claim 31, wherein locating the first position on the interior surface of the biological tissue includes electrophysiological mapping the first interior surface.

33. The method of claim 31, further comprising, after applying the patch, performing a therapeutic procedure on the biological tissue at or in the vicinity of the second position.

34. The method of claim 33, wherein performing the therapeutic procedure comprises ablating a portion of the biological tissue to form a lesion.

35. The method of claim 34, further comprising electrically detecting the lesion on at least one of the interior surface and the exterior surface.

36. A method of performing an operation, the method comprising:

locating a first position on an interior surface of a biological tissue;

using a surgical instrument to apply pressure to the interior surface and create a protrusion on an exterior surface of the biological tissue, the protrusion corresponding to a second position; and applying a marking substance beneath the exterior surface corresponding to the second position.

37. The method of claim 36, wherein locating the first position on the interior surface of the biological tissue includes electrophysiological mapping the first interior surface.

38. The method of claim 36, further comprising, after applying the marking substance, performing a therapeutic procedure on the biological tissue at or in the vicinity of the second position.

39. The method of claim 38, wherein performing the therapeutic procedure comprises ablating a portion of the biological tissue to form a lesion.

40. The method of claim 39, further comprising electrically detecting the lesion on at least one of the interior surface and the exterior surface.

41. The method of claim 36, wherein the marking substance comprises at least one of an ink, a dye, a radionuclide, a radiopaque substance; and a magnetic sub stance.

* * * * *